(12) United States Patent
Schmidt

(10) Patent No.: US 11,260,224 B2
(45) Date of Patent: Mar. 1, 2022

(54) DEEP TISSUE PULSED ELECTROMAGNETIC FIELD THERAPY APPARATUS AND METHOD OF USE THEREOF

(71) Applicant: Traci Schmidt, Phoenix, AZ (US)

(72) Inventor: Traci Schmidt, Phoenix, AZ (US)

(*) Notice: Subject to any disclaimer, the term of this patent is extended or adjusted under 35 U.S.C. 154(b) by 146 days.

(21) Appl. No.: 16/685,935

(22) Filed: Nov. 15, 2019

(65) Prior Publication Data

US 2021/0146131 A1 May 20, 2021

(51) Int. Cl.
*A61N 1/36* (2006.01)
*A61N 1/04* (2006.01)
*A61N 1/32* (2006.01)

(52) U.S. Cl.
CPC ....... *A61N 1/36014* (2013.01); *A61N 1/0496* (2013.01); *A61N 1/3603* (2017.08); *A61N 1/326* (2013.01); *A61N 1/36021* (2013.01)

(58) Field of Classification Search
CPC ............... A61N 1/3603; A61N 1/0496; A61N 1/36021; A61N 1/326; A61N 1/36014
See application file for complete search history.

(56) References Cited

U.S. PATENT DOCUMENTS

2019/0143116 A1* 5/2019 Mowery ............ A61N 1/36034
607/53

FOREIGN PATENT DOCUMENTS

| AU | 2012235947 A1 * | 9/2013 | ............... A61B 5/24 |
| WO | WO2021080867 A1 * | 4/2021 | ......... A61N 1/36021 |

* cited by examiner

*Primary Examiner* — Catherine M Voorhees
(74) *Attorney, Agent, or Firm* — Kevin H. Hazen; Hazen Patent Group, LLC

(57) ABSTRACT

The invention comprises a method and apparatus for delivering electrons to skin of a person, comprising the steps of: (1) attaching a longitudinal length of a flexible electrically conductive tape to the skin of the person, the flexible electrically conductive tape comprising: an electrically conductive strip and an adhesive layer, the adhesive layer comprising a top surface and an adhesive surface, (2) the adhesive surface affixing the electrically conductive strip to the skin, where the adhesive layer comprises a set of apertures therethrough to form longitudinally distributed electrical contact points along a length of the electrically conductive strip; and (3) an energy source delivering electrons, under control of an electrical control circuit of a controller, to the electrical contact points of the flexible electrically conductive tape.

8 Claims, 7 Drawing Sheets

DEEP TISSUE PULSED ELECTROMAGNETIC FIELD THERAPY APPARATUS AND METHOD OF USE THEREOF

BACKGROUND OF THE INVENTION

Field of the Invention

The invention relates generally to a pulsed electromagnetic field therapy device.

Discussion of the Prior Art

Patents related to the current invention are summarized here.

John C. Tepper, et. al., "Pulsed Electromagnetic Field (PEMF) Stimulation Therapy System with Bi-Phasic Coil", U.S. Pat. No. 6,132,362 (Oct. 17, 200) describe a PEMF therapy system using a bi-phasic coil PEMF transducer for generating PEMF stimulation signals.

Problem

There exists in the art a need for targeted delivery of electromagnetic stimulation.

SUMMARY OF THE INVENTION

The invention comprises a targeted deep tissue pulsed electromagnetic field therapy apparatus and method of use thereof.

DESCRIPTION OF THE FIGURES

A more complete understanding of the present invention is derived by referring to the detailed description and claims when considered in connection with the Figures, wherein like reference numbers refer to similar items throughout the Figures.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

DETAILED DESCRIPTION OF THE INVENTION

The invention comprises a method and apparatus for delivering electrons to skin of a person, comprising the steps of: (1) attaching a longitudinal length of a flexible electrically conductive tape to the skin of the person, the flexible electrically conductive tape comprising: an electrically conductive strip and an adhesive layer, the adhesive layer comprising a top surface and an adhesive surface, (2) the adhesive surface affixing the electrically conductive strip to the skin, where the adhesive layer comprises a set of apertures therethrough to form longitudinally distributed electrical contact points along a length of the electrically conductive strip; (3) an energy source delivering electrons, under control of an electrical control circuit of a controller, to the electrical contact points of the flexible electrically conductive tape; (4) serially delivering a first portion of the electrons through first apertures of the set of apertures to a first section of the skin and delivering a second portion of the electrons through second apertures of the set of apertures to a second section of the skin of the person; (5) electrically attaching a contact accessory to the energy source, the contact accessory comprising a contact end, the contact end comprising a rounded surface; and (6) translating the rounded surface of the contact accessory along the longitudinal length of the flexible electrically conductive tape to deliver the electrons through the electrical contact points formed by the set of apertures.

Energy Therapy

Figure 1:
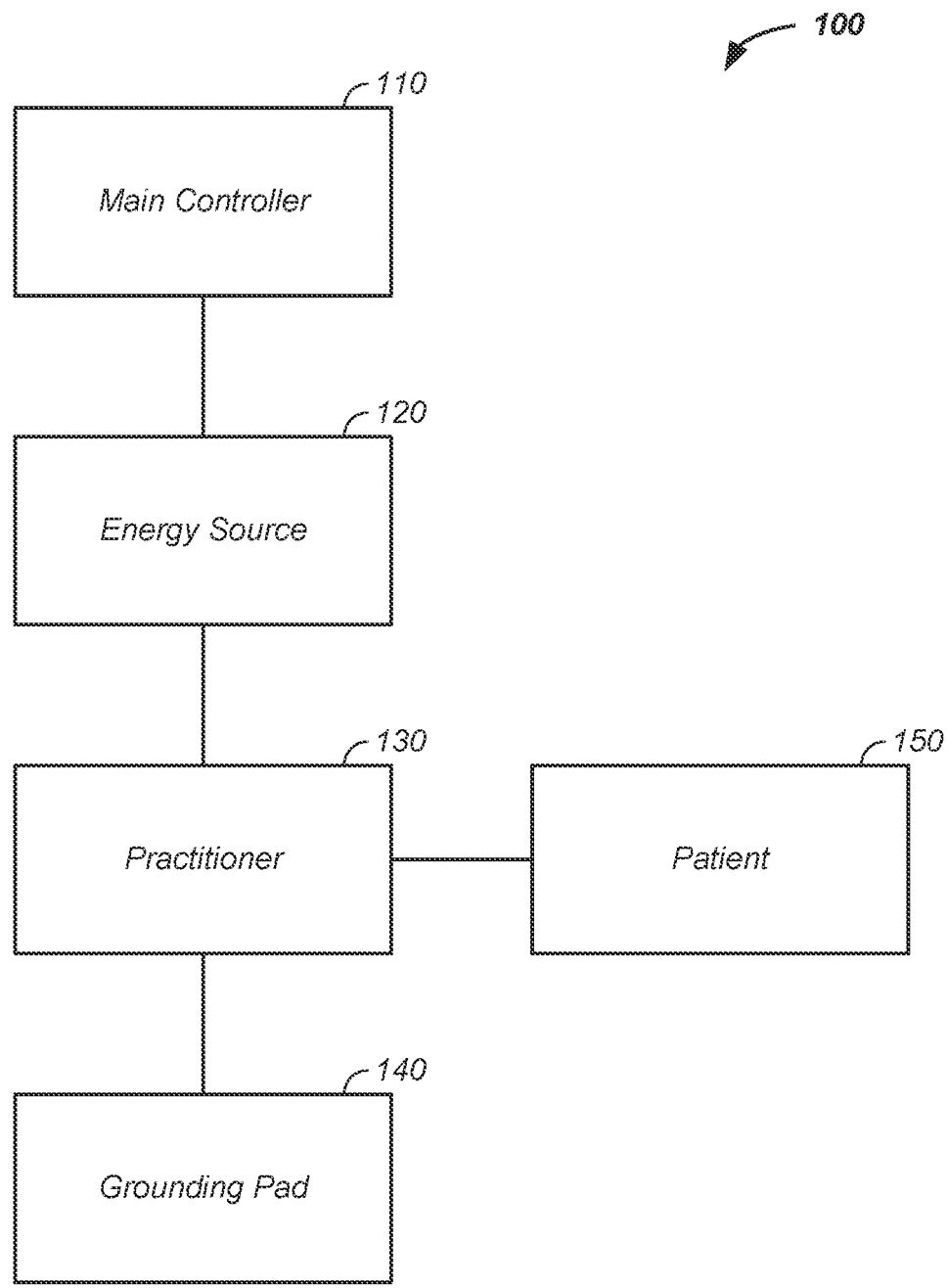
FIG. 1 illustrates a pulsed electromagnetic field therapy apparatus.

Referring now to FIG. 1, an energy stimulation device 100 is illustrated, comprising a main controller 110 and an energy source 120. The energy source 120 is used to deliver electrons, such as in the form of a current with an associated voltage, to a user, a subject, and/or a patient 150. The main controller 110 comprises a circuit controller to control the energy source 120. In one embodiment, the energy stimulation device 100 is an electron delivery device. Generally, the energy stimulation device 100 delivers pulsed electromagnetic stimulation and/or a pulsed electromagnetic field to the body for therapy in the form of an electromagnetic wave, energy, electrons, and/or a voltage. Herein, for clarity of presentation and without loss of generality, the stimulation device is described as delivering electrons, delivering a wave of energy, and/or is referred to as delivering an energy with a corresponding intensity and frequency. Pulsed electromagnetic field therapy uses bursts of low-level electromagnetic radiation and/or flow of electrons to heal damaged tissues and bone, to relieve injury-related pain, and even to stimulate organs, such as: via delivery of electrons and/or energy to mitochondria and/or providing energy that allows the body to heal on its own using its own healing and regeneration abilities at the targeted areas of noninvasive delivery of the energy. Several examples illustrate use of the energy stimulation device 100.

EXAMPLE I

Still referring to FIG. 1, in a first example, a practitioner 130, such as a technician or doctor, is attached to the energy source 120 and a grounding pad 140 of the energy stimulation device. The practitioner 130 delivers electrons from the energy source to the patient 150, such as by a touch conducting the current through the practitioner 130 to the patient 150. For instance, the practitioner 130 traces a nerve line of the patient 130 with a contacting finger/digit and delivers the electrons to the surface of the skin of the patient 130 along a longitudinal length of the nerve line and/or a treatment area.

EXAMPLE II

Figure 2:
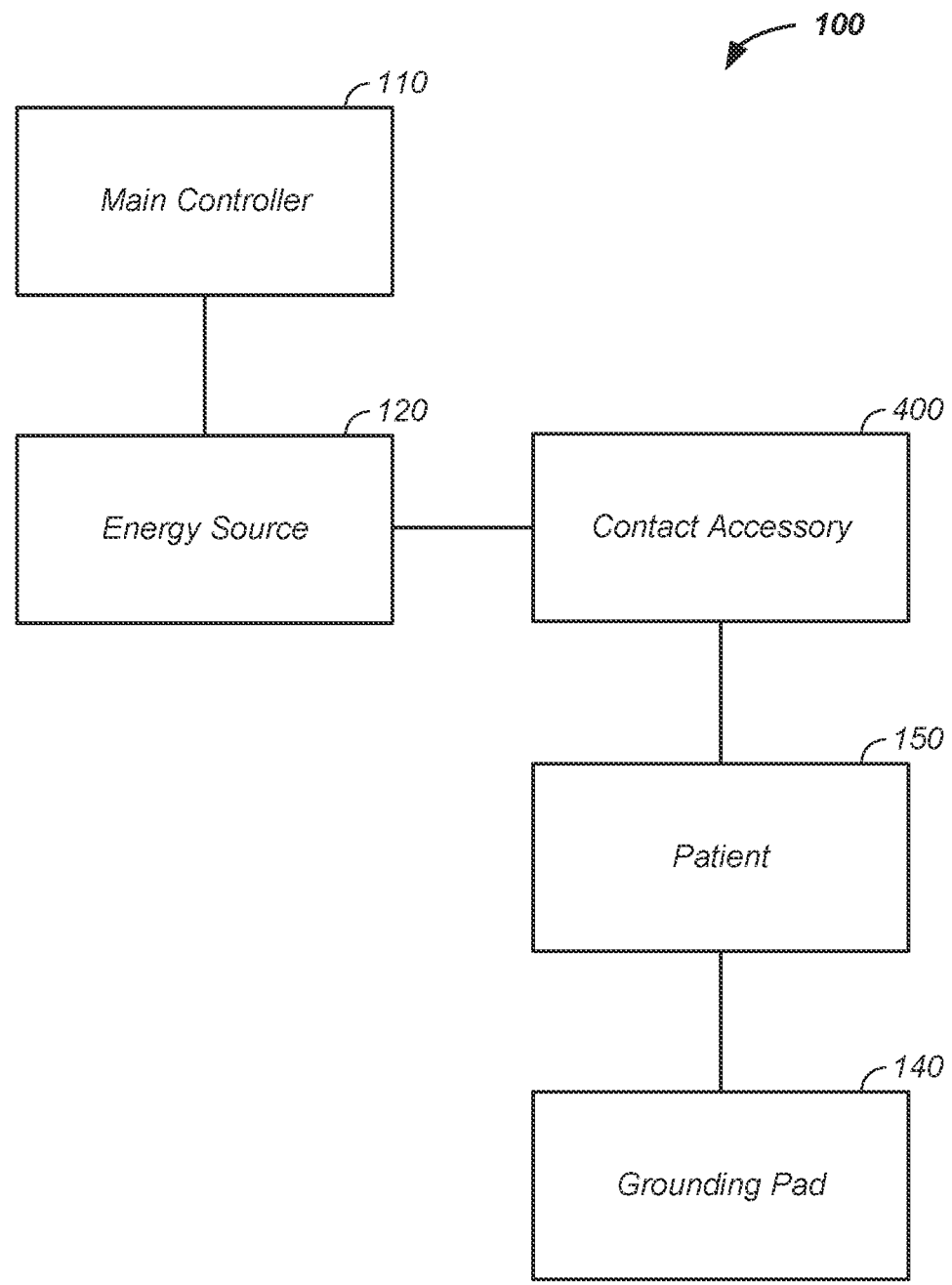
FIG. 2 illustrates a patient controlled treatment apparatus.

Referring now to FIG. 2, a second example of use of the energy stimulation device 100 is illustrated. In this example, the patient 150 self-treats using a contact accessory 400, also referred to as a treatment accessory. In the self-treatment case, the patient 140 is attached to the grounding pad 140 and the electrons are delivered from the energy source 120 via the contact accessory 400 to the patient 150. In this example, the patient 130 touches the contact accessory 400 to a surface area of skin of the patient 130 for treatment. For instance, the patient 150 treats a skin surface area near an organ and/or a skin surface area proximate a damaged portion of their own body.

EXAMPLE III

Figure 3:
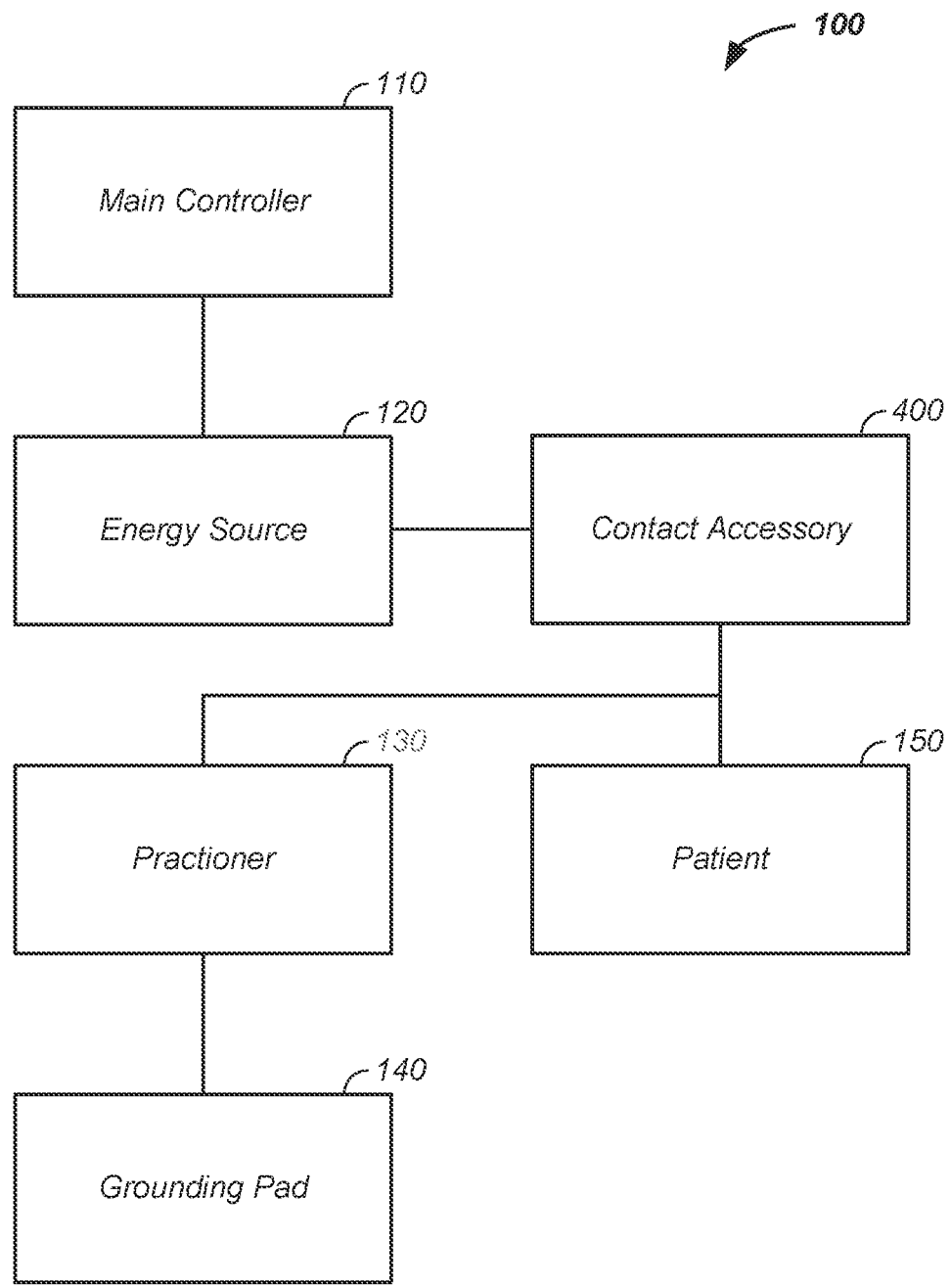
FIG. 3 illustrates a practitioner controlled treatment apparatus.

Referring now to FIG. 3, a third example of use of the energy stimulation device 100 is illustrated. In this example, the practitioner 130 uses the contact accessory 400 to treat the patient 150. In this case, the practitioner 130 and/or the patient 130 is attached to the grounding pad 140 and electrons are delivered from the energy source 120 to the patient 150 via the contact accessory 400, where the contact accessory 400 is guided by the practitioner 130. For instance, the practitioner 130 directs the electron flow, via the contact accessory 400, along a muscle filament and/or along a spasming muscle.

Contact Accessory

Referring now to FIGS. 4(A-H), examples of the contact accessory 400 are provided.

Figure 4A:
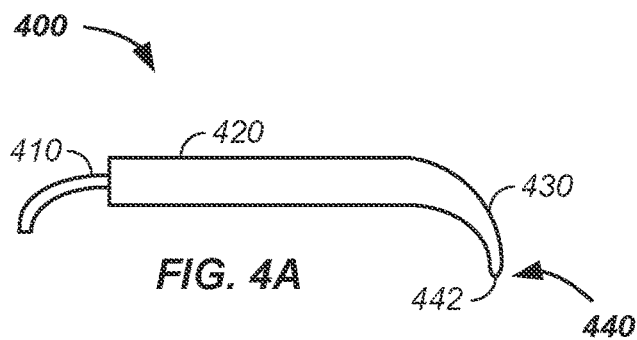
FIG. 4A illustrates a wired treatment accessory.

Referring now to FIG. 4A, a general form of the contact accessory 400 is illustrated with: (1) a connecting wire 410, such as a power cable, electron delivery cable, and/or a control cable connected at a first end to the energy source 120 and at the opposite end to the contact accessory 400; (2) a handle 420, such as for grasping by the practitioner 130 or patient 150; and (3) a treatment end 430, such as having a treatment tip 440 for delivery of the electrons. Optionally and preferably, the treatment tip 440 comprises a rounded end 442 for distribution of the electrons to a treatment zone, treatment area, and/or incident energy delivery area, such as to distribute the electrons to a zone. During use, the electrons pass from the energy delivery area into a volume of the patient 150. For clarity of presentation, the connecting wire 410 is only illustrated on the first contact accessory example in FIG. 4A, though the connecting wire is optionally and preferably attached to any and/or contact accessory, such as by a removably attached plug/power adaptor.

Figure 4B:
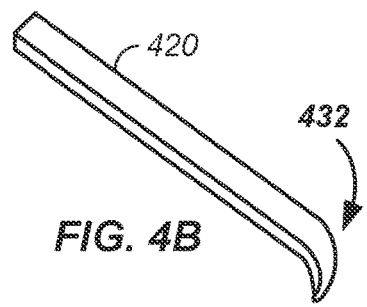
FIG. 4B illustrates a curved tip treatment accessory.

Referring now to FIG. 4B, a second example of a contact accessory 400 is illustrated with an optional curved end 432. The curved end 432 allows for ergonomic treatment of a specified area of the patient 150 by the practitioner 130 and/or by the patient 150 directly.

Figure 4C:
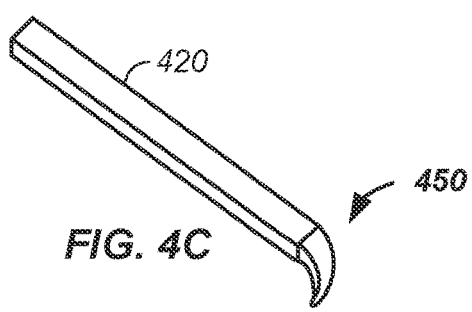
FIG. 4C illustrates a removable tip treatment accessory.

Referring now to FIG. 4C, a third example of a contact accessory 400 for detachable/replaceable/unpluggable attachment to the energy source 120 is provided. In this example, the treatment end 430 of the contact accessory includes an optional removable tip 450. The removable tip 450 allows for exchange with other removable tips with contact surface areas ranging from greater than 0.01, 0.02, 0.05, 0.1, 0.25, 0.5, 1, and 2 square millimeters to less than 10, 5, 2, 1, or 0.5 square centimeters. For a given energy level from the energy source 120, a smaller contact area will deliver a larger treatment dosage to a surface area of skin of the patient 150 connected internally to an internal treatment volume of the patient 150.

Figure 4D:
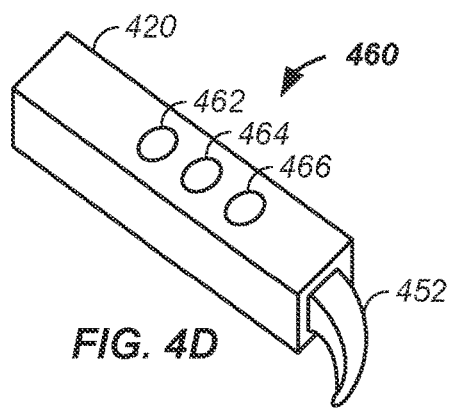
FIG. 4D illustrates a treatment accessory with hand controls.

Referring now to FIG. 4D, a fourth example of a contact accessory 400 is illustrated. As illustrated, the handle 420 of the contact accessory 400 is equipped with an optional claw attachment 452, which is an example of the removable tip 450. The claw attachment 452 allows for strain to be applied by the practitioner 130/patient 150 to the treatment area with application of a pulling force by the practitioner 130/patient 150 while electrons are provided to the treatment area, which is not a viable option with a flat or rounded treatment tip. As illustrated, the handle 420 of the contact accessory 400 is equipped with optional controls 460, such as an on/off control 462, an intensity control 464, and/or a frequency control 466. Additional control buttons, selectors, and/or switches include a duty cycle controller and/or a temperature controller, such as a maintained temperature of at least the treatment tip 440, such as maintained with a heater and controller connected to the controller 110.

Figure 4E:
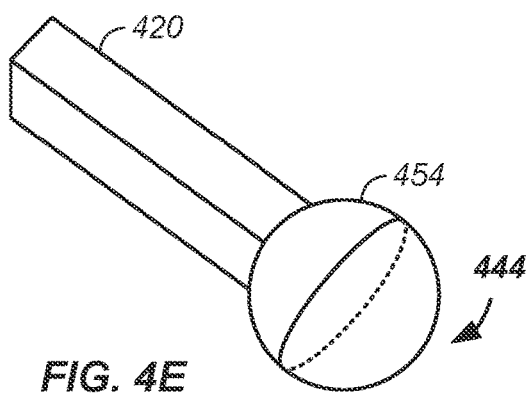
FIG. 4E illustrates a rounded end treatment accessory.

Referring now to FIG. 4E, a fifth example of a contact accessory 400 is illustrated with a rounded head 454 comprising a rounded sample contact zone 444. The rounded sample contact zone 444, which is optionally heated, allows for an applied massaging force 440 by the practitioner 130/patient 150 to the treatment zone. Optionally, the contact accessory 400 and/or a component thereof is equipped with a vibrator, which allows increased blood flow to the treatment volume during treatment with the electrons. The rounded sample contact zone 400 is optionally and preferably translated along a treatment line/treatment curve, such as along a conducting tape as further described, infra.

Figure 4F:
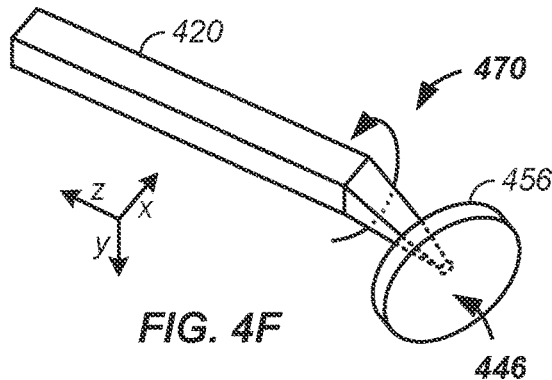
FIG. 4F illustrates a treatment accessory with a rotatable head.

Referring now to FIG. 4F, a sixth example of a contact accessory 400 is illustrated with an optional rotatable/pivotable treatment head 470, such a rotatable with a ball and socket joint and/or rotatable around a longitudinal axis of the handle 420. As illustrated, the contact accessory is provided with an optional flat ended head 456 with a planar delivery surface 446 for delivery of the electrons. Again, the planar delivery surface 446 in combination with the pivotable and/or rotatable treatment head 470 allows for uniform delivery of the electrons along a tracking path, such as along a vein, muscle, and/or nerve, such as through an interfacing conducting tape, as further described infra.

Figure 4G:
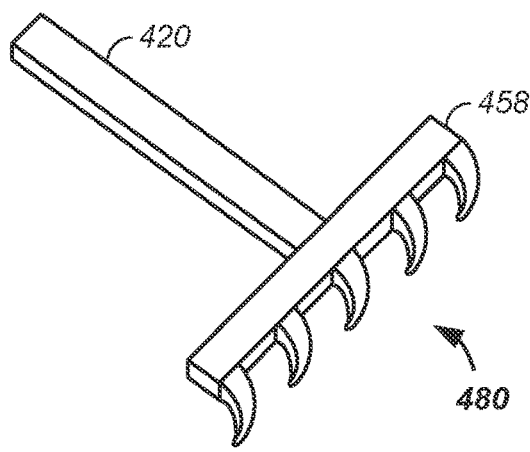
FIG. 4G illustrates a rake treatment accessory.

Referring now to FIG. 4G, a seventh example of a contact accessory 400 is provided with an optional rake accessory. The rake accessory comprises a rake head 458 and rake tines 480. The rake tines, which are used to deliver the electrons is optionally and preferably used over a larger surface area of skin of the patient 150. Current is optionally delivered evenly to each rake tine element of the set of rake times or is delivered to one tine at a time of the rake tines, such a via direction of the main controller 110 and a switching algorithm used to control current flow amongst a series of conductors wired to the individual tines. For example, the switching rate of electron flow between tines is faster than 0.01, 0.05, 0.1, 0.5, 1, 2, 5, or 10 Hertz.

Figure 4H:
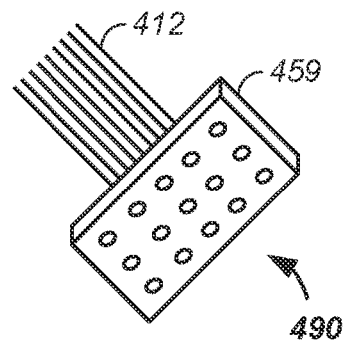
FIG. 4H illustrates a two-dimensional array treatment head.

Referring now to FIG. 4H, an eighth example of a contact accessory is provided with a flat ribbon attached to an optional two-dimensional applicator 459, where x- and/or y-positions of the applicator deliver the electrons at a common time, in a rotating set of lines of applications, and/or in rotating sets of one or more sub-positions/elements 490 of the two-dimensional applicator, such as under control of the main controller 110.

Electrically Conductive Tape

Referring now to FIGS. 5(A-D) and FIGS. 6(A-C) an electrically conductive tape 500 is described. Generally, the electrically conductive tape 500 couples electrons from the practitioner 130 and/or the contact accessory 400 to the patient 150. Generally, the electrically conductive tape 500 is attached to the skin of the patient 150 and the practitioner 130 and/or the contact accessory 400 makes contact with the electrically conductive tape 500 and electrons from through the electrically conductive tape 500 through a treatment zone on the skin.

Figure 7:
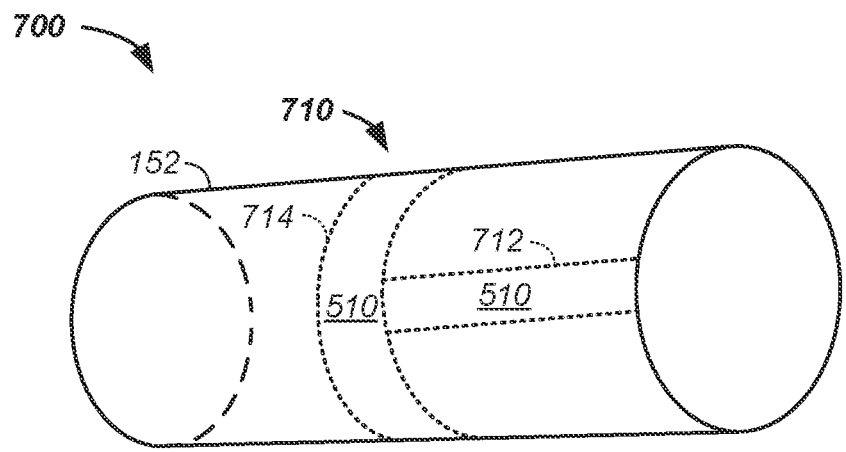
FIG. 7 illustrates a patient/conductive tape interface.
Figure 8:
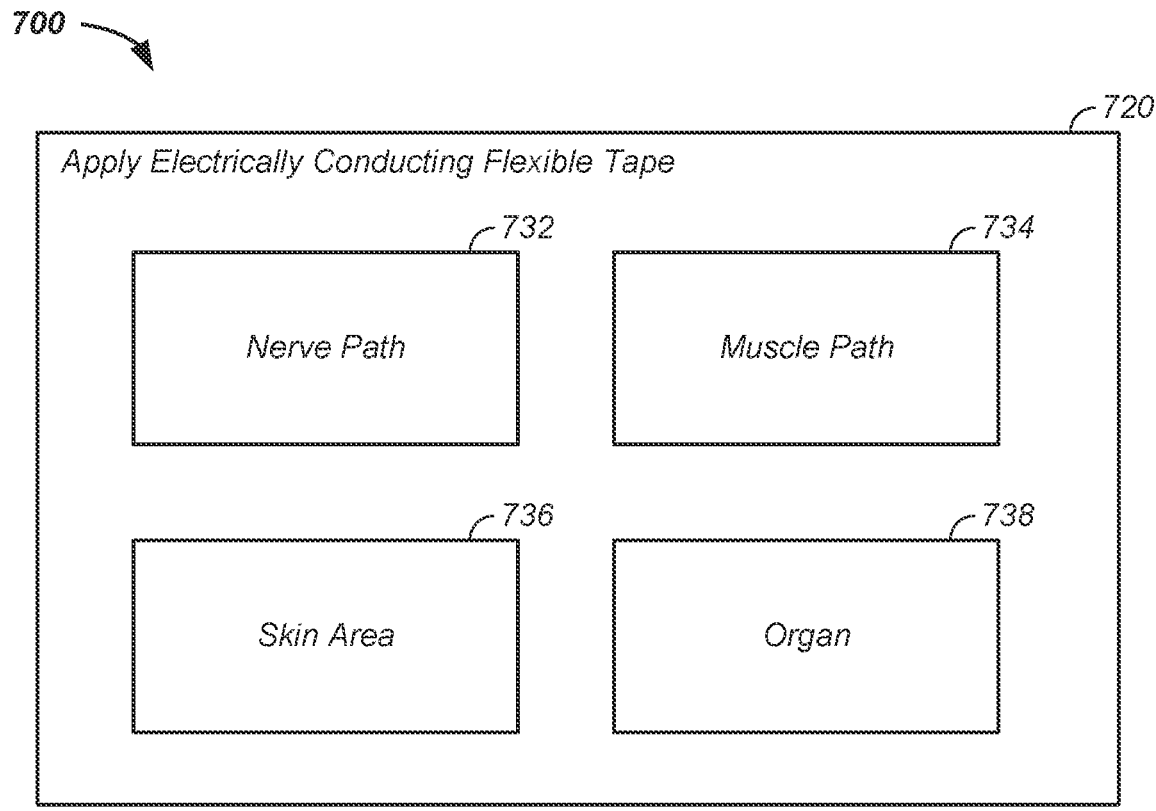
FIG. 8 illustrates application of conductive tape to a user.

Referring now to FIG. 7, an optional method of treatment 700 of a treatment zone 710 of the patient 150 is a method of applying 720 one or more lines 712, one or more arcs 714, and/or one or more geometric patterns of the electrically conductive tape 500 onto the skin 152 of the patient 150. Subsequently, the electrons are brought into contact with the electrically conductive tape, as discussed in the preceding paragraph. Optionally and preferably, the electrically conductive tape is attached to the skin 152 of the patient above and/or longitudinally parallel to a nerve path 732, muscle path 734, skin area 736, and/or an organ 738, such as to provide electrons to the nerve, muscle path, skin area, organ, mitochondria, and/or body constituent.

Referring again to FIGS. 5(A-D) and FIGS. 6(A-C) the electrically conductive tape 500 is further described by way of examples.

Figure 5A:
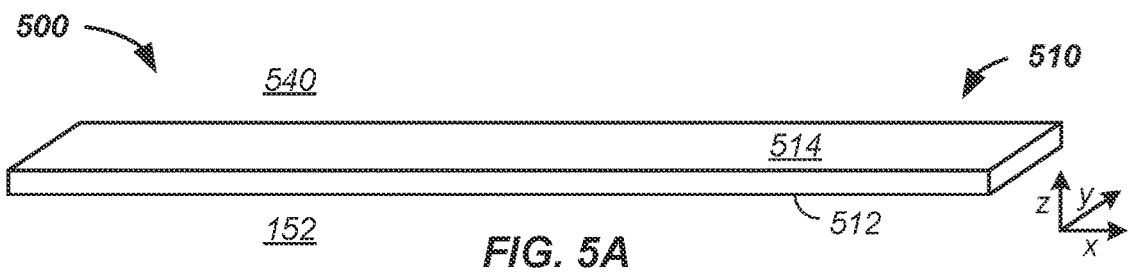
FIG. 5A illustrates a conductive tape.

Referring still to FIG. 5A, generally the electrically conductive tape 500 has a longitudinal axis, such as along an electrically conductive strip 510, with a first side 512 attached to the skin 152 of the patient 150 and a second side 514, such as in contact with air 540. As illustrated, the electrically conductive tape 500 has a width along the y-axis, such as a width greater than 1, 2, 3, and/or 4 millimeters and less than 50, 40, 30, 20, 10, and/or 5 millimeters. The first side 512, the tissue contacting side, optionally and preferably has an adhesive component covering at least a portion of the first side.

Figure 5B:
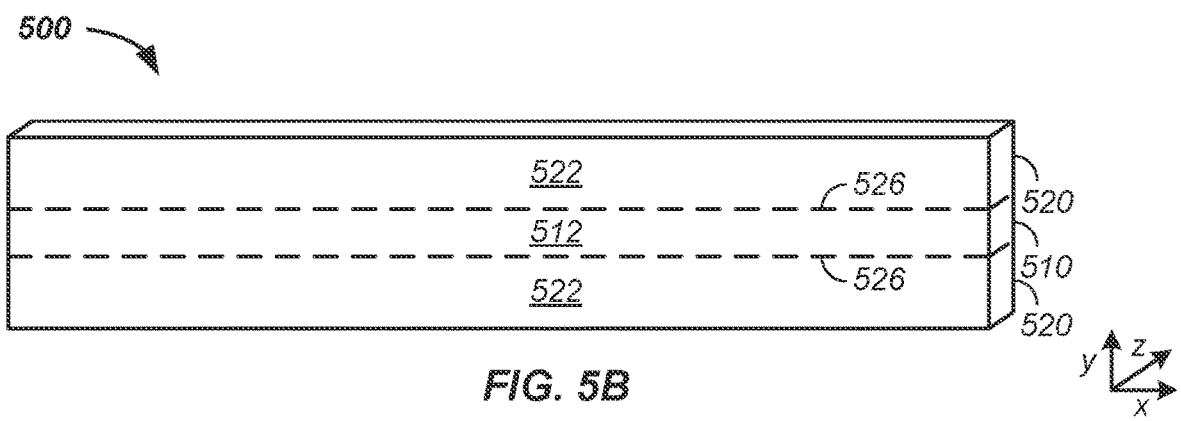
FIG. 5B illustrates a self-adhesive conductive tape.

Referring to FIG. 5B, a second example of the electrically conductive tape 500 is provided. As illustrated, the electrically conductive tape contains one or more electrically conductive strips 510 and/or one or more optionally electrically conductive longitudinal sections, where the one or more electrically conductive segments are separated by connecting wires and/or electrically insulating zones. As illustrates, the electrically conductive strip 510 is positioned between a pair of longitudinal adhesive strips 520, such as with an adhesive side 522. Optionally, the pair of longitudinal adhesive strips 520 longitudinally attach to opposite edges of the electrically conductive strip 510, such as along a pair of interface lines 526. In this example, the pair of longitudinal adhesive strips 520 aid in contact of the electrically conductive strip 510 with the skin 152 of the patient 150 during use. Optionally, an electrically conductive gel is used to couple the electrically conductive tape 500 and/or the electrically conductive strip 510 to the skin 152 of the patient 150 during use. Notably, the electrically conductive strip 510 with insulators on either side, such as the longitudinal adhesive strips 520, directs electron flow into the taped lines and/or taped paths. Hence, the electrons flow into the skin 152 of the patient along lines or paths that follow the underlying nerves and/or muscles. As the width of the electrically conductive tape 500 is both defined and narrow, electron flow to adjoining, radially outward, areas is restricted. Hence, a jitter of the practitioner's hand and/or a shake of the contact accessory 400 into regions adjoining the electrically conductive strip 510 does not direct electrons to non-targeted areas. Indeed, small errors in tracking of the contact accessory 400 along the electrically conductive strip 510 still results in full flow of the electrons into the targeted paths as the electrically conducting head, such as the treatment tip 440, rounded sample contact zone 444, and/or the planar delivery surface 446 still deliver the electrons solely to the electrically conductive strip 510 as long as the edges of the treatment tip 440 do not stray all the way past the, optionally wide, longitudinal adhesive strips 520. The longitudinal adhesive strips are optionally greater than 1, 2, 5, 10, 15, 20, 30, 40, or 50 millimeters wide and/or have a combined width greater than 1.5, 2, 3, 5, 10, 20, or 50 times a width of the treatment tip 440. One example of acceptable jitter of the practitioner's delivery hand and/or acceptable jitter of the treatment tip 440 is a y-axis movement across the electrically conductive tape 500 within the y-axis width of the tape, such as a delta-y movement of less than 2, 4, 6, 8, or ten millimeters per inch of travel along the x-axis length of the electrically conductive tape 500.

Still referring to FIG. 5B, the electrically conductive strip 510 is optionally a flat conducting wire. However, the electrically conductive strip 510 is optionally and preferably a substrate embedded with a conductor, such as a conductor containing a chemical form of copper, aluminum, silver, nickel, an electrically conductive polymer, and/or graphite. The electrically conductive strip is optionally an anisotropic x-axis and/or z-axis electrical conductor, such as in an acrylic based adhesive. The anisotropic x-axis electrical tape carries current along the length of the tape, an anisotropic z-axis electrical tape will carry current through the height of the tape along the z-axis. An example of an anisotropic electrical tape is z-axis conductive tape 9703 manufactured by 3M (Maplewood, Minn.).

Figure 5C:
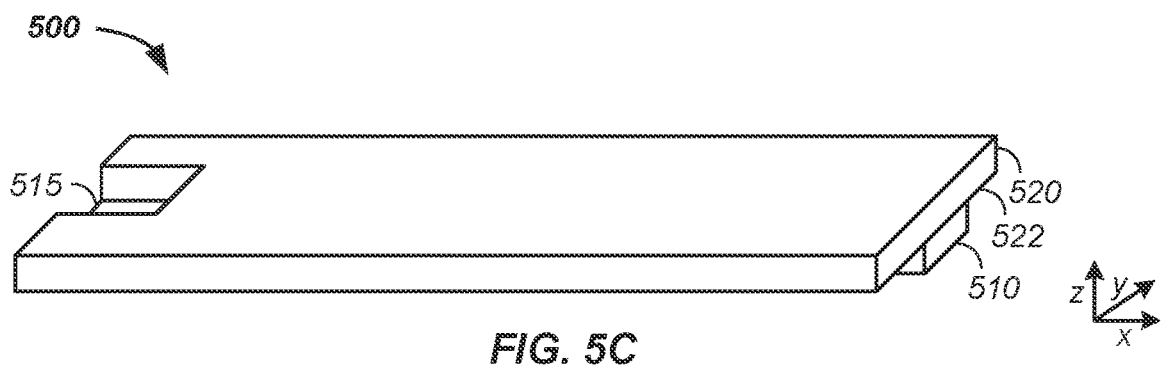
FIG. 5C illustrates a tab accessible conductive tape.

Referring now to FIG. 5C, a third example of the electrically conductive tape 500 is provided. As illustrated, the electrically conductive strip 510 is attached on a back side to an optionally adhesive strip 520, such as an adhesive layer. The adhesive strip 520 attached with an adhesive side 522 to the skin 152 of the patient 150 holds the electrically conductive strip 522 in contact with the skin 152. To provide a contact point with the practitioner 130 and/or the contact accessory 400, to allow flow of the electrons, one or more contact tabs 515 and/or apertures are cut through the adhesive strip 520.

Figure 5D:
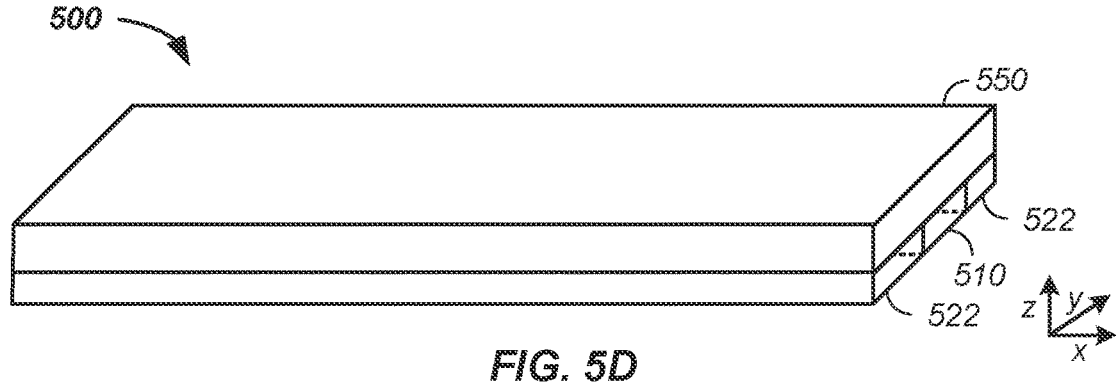
FIG. 5D illustrates a dual layer conductive tape.

Referring now to FIG. 5D, a fourth example of the electrically conductive tape 500 is provided. In this example, an optionally electrically conductive layer 550 contacts the electrically conductive strip 510, which provides a conductive route for the electrons to flow from the practitioner 130 and/or the energy source 120 to the skin 152 of the patient 150. Further, the electrically conductive layer 500 functions as a support matrix for an adhesive and/or one or more adhesive strips 522 used to affix the electrically conductive tape 500 to the skin 152 of the patient 150.

Still referring to FIGS. 5(A-D), the electrically conductive tape is optionally kinesio-type tape, also known as KT-tape, that has been modified to include an electrically conductive strip 510 and/or an electrically conductive layer 550. As such, the electrically conductive tape 500 is optionally applied as KT-tape, such as to support ligaments and capsules of unstable joints by limiting excessive or abnormal anatomical movement; to enhance proprioceptive feedback from the limb or joint; to stabilize and support joints after injuries to a muscle and/or a ligament; to prevent neuromuscular damage; to reduce force to a treatment area; and/or to support injuries at the muscle-tendon units by compressing and limiting movement and secure protective pads, dressings and splints. Notably, KT-taping along the nerve tract of irritated and/or inflamed tissue shortens the inflamed region and reduces pain at the same time using benefits of the KT-tape at the same time the electrically conductive strip 510 in the electrically modified KT-tape delivers healing electrons and/or electromagnetic waves to the tissue. Generally, taping with electrically conductive strip 510 modified KT-tape is a process of applying tape directly to the skin in order to maintain a stable position of bones and muscles, such as during athletic activity. Further, the electrically conductive strip modified KT-tape is attached to the skin to physically hold muscles or bones at a certain position.

Figure 6A:
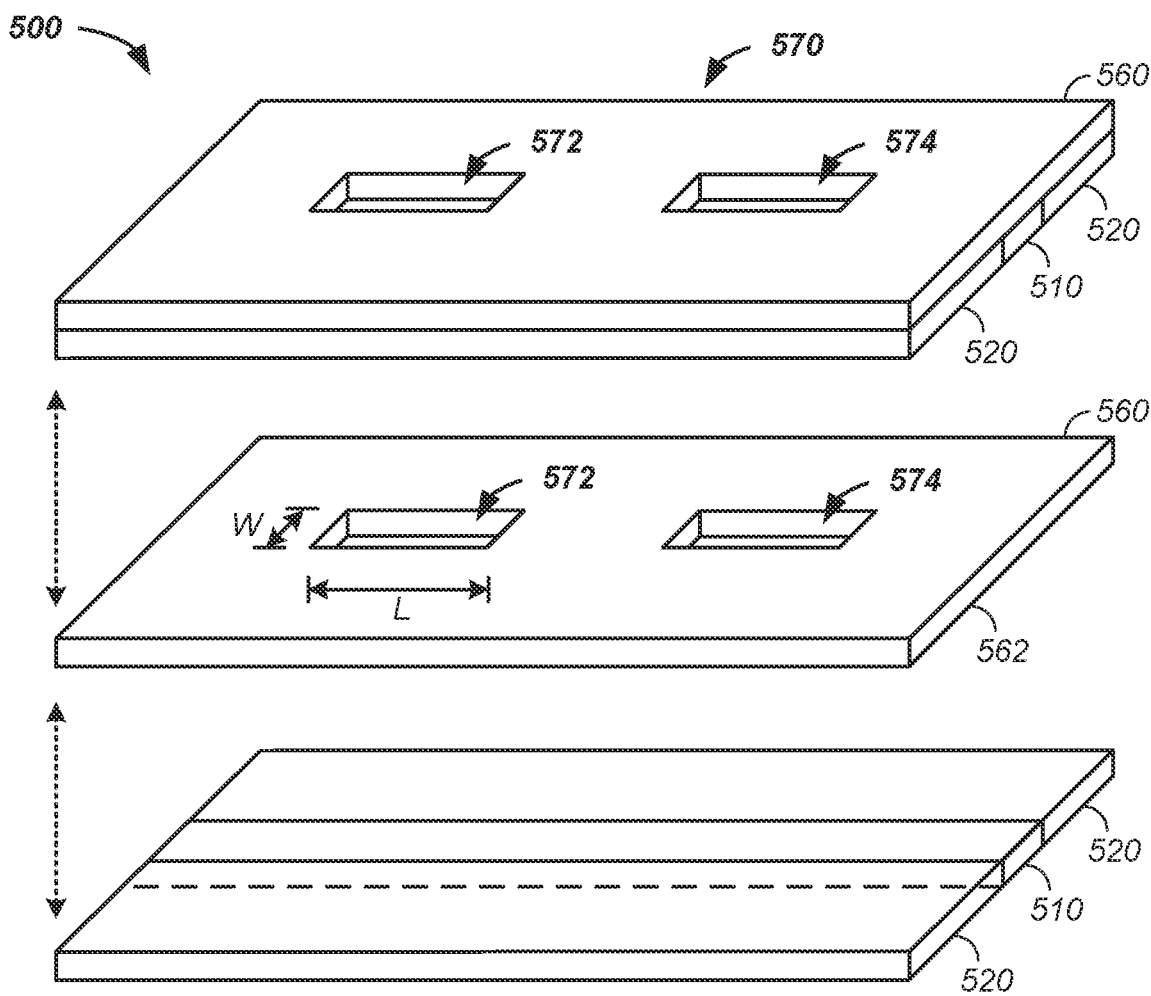
FIG. 6A illustrates an exploded view of a conductive tape.

Referring now to FIG. 6A, a fifth example of the electrically conductive tape 500 is provided in an exploded view. As illustrated, the electrically conductive strip 510 longitudinally connects with a backing layer 560 having a conductor strip contacting side 562. The backing layer 560 contains one or more holes, openings, slot, cuts, indentations, and/or apertures 570 therethrough. As illustrated, a first aperture 572 and a second aperture 574 through the backing layer 560 allow for contact of the practitioner 130, contact accessory 400, treatment tip 440, rounded sample contact zone 444, and/or the planar delivery surface 446, which allows flow of electrons to the skin 152 of the patient 150. Optionally, there are greater than 0, 1, 2, 3, 5, 10, 20, or 50 apertures 570 per unit length of the electrically conductive tape 500 where a unit length of the electrically conductive tape is one inch. The apertures 570 are optionally of any geometric shape. For clarity of presentation, the apertures are illustrated with a length and an width, where individual aperture opening dimensions are greater than 0.01, 0.1, or 1 millimeter along a given x-axis and/or y-axis. As illustrated one or more optional adhesive strips 520 and/or adhesives, backed by the backing layer 560, are used to temporarily and removably affix the electrically conductive tape 500 to the skin 152 of the patient 150.

Still referring to FIG. 6A, during use the contact of the practitioner 130, contact accessory 400, treatment tip 440, rounded sample contact zone 444, and/or the planar delivery surface 446 deliver the electrons through a limited number of apertures 570 at one time, such as a number of apertures in a 1, 0.9, 0.8, 0.7, 0.6, 0.5, 0.4, 0.3, 0.2, and/or 0.1 unit length. In this manner, all of the electrons from the energy source 120 delivered to the skin 152 of the patient 150 are delivered to a small area as a function of time and, notably, are evenly distributed, as opposed to the case of electrons being spread out over a contact area of the practitioner 130 with the patient 150 and/or being delivered to a short length of a long length of the electrically conductive tape 500.

Figure 6B:
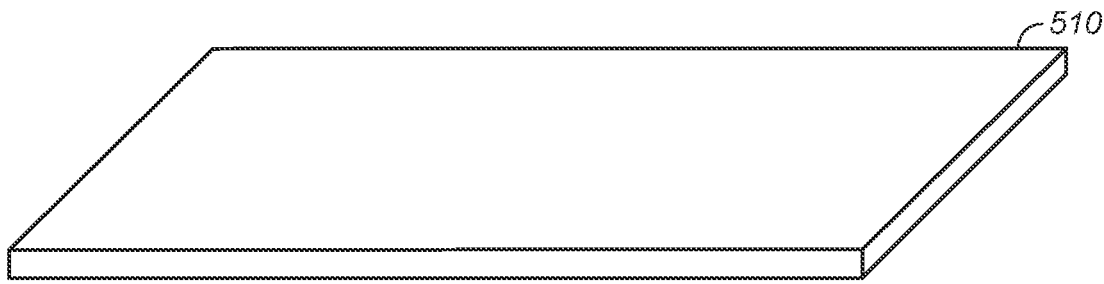
FIG. 6B illustrates a broad conductive tape.
Figure 6C:
FIG. 6C illustrates a narrow conductive tape.

Referring now to FIG. 6B and FIG. 6C, varying widths of the electrically conductive strip 510, such as greater than 0.1, 0.2, 0.5, and/or 1 millimeter and less than 30, 20, or 10 millimeters.

Still yet another embodiment includes any combination and/or permutation of any of the elements described herein.

The main controller/controller/system controller, a localized communication apparatus, and/or a system for communication of information optionally comprises one or more subsystems stored on a client. The client is a computing platform configured to act as a client device or other computing device, such as a computer, personal computer, a digital media device, and/or a personal digital assistant. The client comprises a processor that is optionally coupled to one or more internal or external input device, such as a mouse, a keyboard, a display device, a voice recognition system, a motion recognition system, or the like. The processor is also communicatively coupled to an output device, such as a display screen or data link to display or send data and/or processed information, respectively. In one embodiment, the communication apparatus is the processor. In another embodiment, the communication apparatus is a set of instructions stored in memory that is carried out by the processor.

The client includes a computer-readable storage medium, such as memory. The memory includes, but is not limited to, an electronic, optical, magnetic, or another storage or transmission data storage medium capable of coupling to a processor, such as a processor in communication with a touch-sensitive input device linked to computer-readable instructions. Other examples of suitable media include, for example, a flash drive, a CD-ROM, read only memory (ROM), random access memory (RAM), an application-specific integrated circuit (ASIC), a DVD, magnetic disk, an optical disk, and/or a memory chip. The processor executes a set of computer-executable program code instructions stored in the memory. The instructions may comprise code from any computer-programming language, including, for example, C originally of Bell Laboratories, C++, C#, Visual Basic® (Microsoft, Redmond, Wash.), Matlab® (MathWorks, Natick, Mass.), Java® (Oracle Corporation, Redwood City, Calif.), and JavaScript® (Oracle Corporation, Redwood City, Calif.).

The main controller/controller/system controller comprises computer implemented code to control one or more sub-systems. The computer implemented code is programmed in any language by one skilled in the art of the subsystem and/or by a skilled computer programmer appropriate to the task. Herein, for clarity of presentation and without loss of generality, specific computer code is not presented, whereas computer code appropriate to the task is readily available commercially and/or is readily coded by a computer programmer with skills appropriate to the task when provided the invention as described herein.

Herein, any number, such as 1, 2, 3, 4, 5, is optionally more than the number, less than the number, or within 1, 2, 5, 10, 20, or 50 percent of the number.

Herein, an element and/or object is optionally manually and/or mechanically moved, such as along a guiding element, with a motor, and/or under control of a main controller.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for delivering electrons to skin of a person, comprising the steps of:
attaching a longitudinal length of a flexible electrically conductive tape to the skin of the person, said flexible electrically conductive tape comprising:
an electrically conductive strip;
an adhesive layer, said adhesive layer comprising a top surface and an adhesive surface, said adhesive surface affixing said electrically conductive strip to the skin,
wherein said adhesive layer comprises a set of apertures therethrough to form longitudinally distributed electrical contact points along a length of said electrically conductive strip; and
an energy source delivering electrons, under control of an electrical control circuit of a controller, to said electrical contact points of said flexible electrically conductive tape;
electrically attaching a contact accessory to said energy source, said contact accessory comprising a contact end, said contact end comprising a rounded surface; and
translating said rounded surface of said contact accessory along said longitudinal length of said flexible electrically conductive tape to deliver the electrons through said electrical contact points formed by said set of apertures.

2. The method of claim 1, further comprising the step of:
serially delivering a first portion of the electrons through first apertures of the set of apertures to a first section of the skin and delivering a second portion of the electrons through second apertures of the set of apertures to a second section of the skin of the person.

3. The method of claim 1, further comprising the steps of:
passing at least ninety percent of the electrons through the set apertures to said electrical contact points in the presence of jittery control of said contact end of said contact accessory, where the jittery control comprises longitudinal movement of said contact end along said flexible electrically conductive tape in sequential contacts with sub-sets of the electrical contact points while allowing radial shake of the contact end up to a width of said adhesive layer, said adhesive layer comprising an electrical insulating barrier, said width of said adhesive layer comprising less than two inches.

4. The method of claim 1, further comprising the steps of:
attaching said flexible electrically conductive tape along a nerve path of the person; and
the person translating said contact end of said contact accessory along said longitudinal length of said flexible electrically conductive tape to deliver the electrons to said longitudinally distributed electrical contact points to self-treat the nerve path with the electrons from the energy source.

5. The method of claim 1, further comprising the steps of:
supporting at least one of a muscle and a ligament of the person with said flexible electrically conductive tape, said flexible electrical conductive tape further comprising a kinesio-type tape.

6. The method of claim 1, further comprising the step of:
pivoting a treatment head of said contact accessory about a pivot joint between a handle end of said contact accessory and said treatment head.

7. The method of claim 1, further comprising the step of:
applying kinesiology tape to the skin to support at least one of a muscle and a ligament of the person, said flexible electrically conductive tape embedded into said kinesiology tape.

8. The method of claim 7, further comprising the step of:
applying an electrically conductive gel layer to the skin of the person between the skin and said flexible electrically conductive tape.

* * * * *